(12) United States Patent
Shimada et al.

(10) Patent No.: US 9,982,288 B2
(45) Date of Patent: May 29, 2018

(54) MUCOPOLYSACCHARIDOSIS IVA/VII SCREENING AND TREATMENT METHOD

(71) Applicant: THE NEMOURS FOUNDATION, Jacksonville, FL (US)

(72) Inventors: Tsutomu Shimada, Wilmington, DE (US); Shunji Tomatsu, Wilmington, DE (US)

(73) Assignee: THE NEMOURS FOUNDATION, Jacksonville, FL (US)

( * ) Notice: Subject to any disclaimer, the term of this patent is extended or adjusted under 35 U.S.C. 154(b) by 195 days.

(21) Appl. No.: 14/700,667

(22) Filed: Apr. 30, 2015

(65) Prior Publication Data

US 2015/0315626 A1 Nov. 5, 2015

Related U.S. Application Data

(60) Provisional application No. 61/986,368, filed on Apr. 30, 2014.

(51) Int. Cl.
*C12Q 1/34* (2006.01)
*C12Q 1/527* (2006.01)
*C12Q 1/44* (2006.01)

(52) U.S. Cl.
CPC ............. *C12Q 1/527* (2013.01); *C12Q 1/34* (2013.01); *C12Q 1/44* (2013.01); *G01N 2333/916* (2013.01); *G01N 2333/938* (2013.01); *G01N 2400/40* (2013.01); *G01N 2800/042* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 2006/0286034 A1* | 12/2006 | Meikle | G01N 33/66 424/9.2 |
| 2011/0008810 A1 | 1/2011 | Tomatsu et al. | |
| 2015/0099789 A1* | 4/2015 | Masson | A61K 31/7048 514/432 |

OTHER PUBLICATIONS

Lee G. et al. Enzymatic Studies of Urinary Isomeric Chondroitin Sulfates from Patients with MPS. Clinica Chimica Acta 104(1)65-75, May 21, 1980. (Year: 1980).*
Oguma T. et al. Analytical Method for the Determination of Disaccharides Derived from Keratan, Heparan and Dermatan Sulfates . . . Analytical Biochemistry 368:79-86, 2007. (Year: 2007).*
Tomatsu S. et al. Keratan Sulphate Levels in MPS and Mucolipidoses. J Inherit Metab Dis 28:187-202, 2005. (Year: 2005).*
Hytonen M. et al. A Novel GUSB Mutation in Brazilian Terriers . . . PLoS One 7(7)1-11, Jul. 2012. (Year: 2012).*
Kodama C. et al. HPLC of Pyridylamino Dervatives of Unsaturated Disaccharides . . . J of Biochemistry 96(4)1283-7, Oct. 1984. (Year: 1984).*
Dũng et al., "Mucopolysaccharidosis IVA: correlation between genotype, phenotype and keratan sulfate levels", *Mol Genet. Metab.*, vol. 110, pp. 129-138 (2013).
Haskins et al., "β-glucuronidase deficiency in a dog: a model of human mucopolysaccharidosis VII", *Pediatr. Res.*, vol. 18, No. 10, pp. 980-984 (1984).
Hata et al., "A rapid and micro method for separation of acidic glycosaminoglycans by two-dimensional electrophoresis", *Anal. Biochem.*, vol. 45, pp. 462-468 (1972).
Hopwood et al., "High-resolution electrophoresis of urinary glycosaminoglycans: an improved screening test for the mucopolysaccharidoses", *Anal. Biochem.*, vol. 119, pp. 120-127 (1982).
Imanari et al., "High-performance liquid chromatographic analysis of glycosaminoglycan-derived oligosaccharides", *J. Chromatogr. A*, vol. 720, pp. 275-293 (1996).
Koshiishi et al., "Enzymatic method for the simultaneous determination of hyaluronan and chondroitin sulfates using high-performance liquid chromatography", *Anal. Biochem.*, vol. 265, pp. 49-54 (1998).
Lamari et al., "Analysis of glycosaminoglycan-derived disaccharides in biologic samples by capillary electrophoresis and protocol for sequencing glycosaminoglycans", *Biomed. Chromatogr.*, vol. 16, pp. 95-102 (2002).
Linhardt et al., "Analysis of glycosaminoglycan-derived oligosaccharides using reversed-phase ion-pairing and ion-exchange chromatography with suppressed conductivity detection", *Anal. Biochem.*, vol. 181, pp. 288-296 (1989).
Oguma et al., "Analytical method of chondroitin/dermatan sulfates using high performance liquid chromatography/turbo ionspray ionization mass spectrometry: application to analyses of the tumor tissue sections on glass slides", *Biomed. Chromatogr.*, vol. 15, pp. 356-362 (2001).
Oguma et al., "Analytical method for the determination of disaccharides derived from keratan, heparan, and dermatan sulfates in human serum and plasma by high-performance liquid chromatography/turbo ionspray ionization tandem mass spectrometry", *Anal. Biochem.*, vol. 368, pp. 79-86 (2007a).
Tomatsu et al., "Mucopolysaccharidosis type VII: characterization of mutations and molecular heterogeneity", *Am. J. Hum. Genet.* vol. 48, pp. 89-96 (1991).
Tomatsu et al., "Development and testing of new screening method for keratan sulfate in mucopolysaccharidosis IVA", *Pediatr. Res.*, vol. 55, No. 4, pp. 592-597 (2004).
Tomatsu et al., "Heparan sulfate levels in mucopolysaccharidoses and mucolipidoses", *J. Inherit. Metab. Dis.*, vol. 28, pp. 743-757 (2005b).

(Continued)

*Primary Examiner* — Ralph J Gitomer
(74) *Attorney, Agent, or Firm* — Drinker Biddle & Reath LLP (57) ABSTRACT

Provided is a rapid screening method for detecting mucopolysaccharidosis IVA and mucopolysaccharidosis VII. Biological samples containing glycosaminoglycans are enzymatically digested to converts chondroitin 6-sulfate into ΔDi-6S. ΔDi-6S is assayed by liquid chromatography-tandem mass spectroscopy analysis. Elevated ΔDi-6S, and thus elevated chondroitin 6-sulfate present in the sample, indicates a likelihood that the test subject is afflicted with mucopolysaccharidosis IVA or mucopolysaccharidosis VII.

25 Claims, 3 Drawing Sheets

(56) References Cited

OTHER PUBLICATIONS

Tomatsu et al., "Validation of disaccharide compositions derived from dermatan sulfate and heparan sulfate in mucopolysaccharidoses and mucolipidoses II and III by tandem mass spectrometry", *Mol. Genet. Metab.*, vol. 99, pp. 124-131 (2010a).
Oguma et al., "Analytical method for determination of disaccharides derived from keratan sulfates in human serum and plasma by high-performance liquid chromatography/turbo-ionspray ionization tandem mass spectrometry", *Biomed. Chromatogr.*, vol. 21, pp. 356-362 (2007b).
Tomatsu et al., "Dermatan sulfate and heparan sulfate as a biomarker for mucopolysaccharidosis I", *J. Inherit. Metab. Dis.*, vol. 33, pp. 141-150 (2010b).
Tomatsu et al., "Newborn screening and diagnosis of mucopolysaccharidoses", *Mol. Genet. Metab.*, vol. 110, pp. 42-53 (2013a).
Tomatsu et al., "Therapies of Mucopolysaccharidosis IVA (Morquio A Syndrome)", *Expert Opinion on Orphan Drugs*, vol. 1, No. 10, pp. 805-818 (2013b).
Whitham et al., "An improved method for the structural profiling of keratan sulfates: analysis of keratan sulfates from brain and ovarian tumors", *Glycobiology*, vol. 9, No. 3, pp. 285-291 (1999).
Tomatsu et al., "Validation of keratan sulfate level in mucopolysaccharidosis type IVA by liquid chromatography-tandem mass spectrometry", *J. Inherit. Metab. Dis.*, DOI 10.1007/s10545-009-9013-x, pp. 1-8 (2010).
Tomatsu et al., "Mucopolysaccharidosis Type IVA (Morquio A Disease): Clinical Review and Current Treatment: A Special Review", *Current Pharmaceutical Biotechnology*, vol. 12, No. 5, pp. 1-15 (2011).

\* cited by examiner

MUCOPOLYSACCHARIDOSIS IVA/VII SCREENING AND TREATMENT METHOD

CROSS REFERENCE TO RELATED APPLICATION

This application claims the benefit of U.S. Provisional Application No. 61/986,368, filed Apr. 30, 2014, the entire disclosure of which is incorporated herein by reference.

REFERENCE TO GOVERNMENT GRANT

The invention was made with government support under grant Nos. P20GM103464 and 1R01HD065767-02 awarded by the National Institutes of Health. The government has certain rights in the invention.

FIELD OF THE INVENTION

The invention relates to screening for mucopolysaccharidosis IVA and VII, and treatment thereof.

BACKGROUND OF THE INVENTION

Mucopolysaccharidoses and its Diagnosis

Mucopolysaccharidoses (MPS) are a family of inheritable metabolic disorders caused by deficiency of lysosomal enzymes required for degradation of glycosaminoglycans (GAGs). Each known MPS type involves deficiency of a specific lysosomal enzyme required for the stepwise degradation of specific GAGs. GAGs include, for example, chondroitin sulfate (CS), dermatan sulfate (DS), heparan sulfate (HS) and keratan sulfate (KS).

Mucopolysaccharidosis IVA (MPS IVA; Morquio A syndrome) is caused by the deficiency of N-acetylgalactosamine-6-sulfate sulfatase (GALNS) resulting in accumulation of chondroitin 6-sulfate (C6S) and KS, mainly in cartilage and its extracellular matrix. MPS IVB is caused by deficiency of β-galactosidease, leading to accumulation of KS but not C6S. Clinically, a classic (severe) form of MPS IVA is characterized by systemic skeletal dysplasia such as short trunk dwarfism, kyphoscoliosis, coxa valga, odontoid hypoplasia, abnormal gait, joint mobility problems, restriction of chest wall movement, and a life span of 20-30 years. Patients with an attenuated form can have a nearly normal life span, with mild involvement of the skeleton. See e.g., Dung et al., (2013), *Mol Genet Metab* 110:129-138. In general, patients with MPS IVB have a milder phenotype of skeletal dysplasia compared with a severe form of MPS IVA.

Mucopolysaccharidosis VII (MPS VII; Sly syndrome) is caused by a deficiency in β-D-glucuronidase. Patients with MPS VII have accumulation of HS, DS, chondroitin-4-sulfate (C4S), and C6S in various tissues and show coarse facial features, mental retardation, short stature, hepatomegaly, bony deformities, GAG excretion, and striking metachromatic granules in peripheral leukocytes (Sly et al. (1973), *J Pediatr* 82:249-257; Tomatsu et al. (1991), *Am J Hum Genet* 48:89-96).

Currently, conventional screening methods for MPS are dye-spectrometric methods such as dimethylmethylene blue (DMB) and alcian blue, to measure total GAGs from urine samples. When such urine assays provide positive results, a definitive diagnosis is determined by measuring enzyme activities in white blood cells or fibroblasts. However, current enzyme activity methods cannot be applied to blood and/or tissue extracts without prior protease, nuclease or hyaluronidase treatment. Moreover, total GAGs in urine does not reflect severity of the neurological or skeletal signs and symptoms and substantial overlapping of the total urine GAG level between the age-matched controls and MPS IV patients is observed, resulting in misdiagnosis of the patients.

Methods for measuring specific GAGs in blood by ELISA (Tomatsu et al. (2004), *Pediatr Res* 55:592-597; Tomatsu et al. (2005), *J Inherit Metab Dis* 28:187-202) or HPLC (Linhardt et al. (1989), *Anal Biochem* 181:288-296; Whithman et al. (1999), *Glycobiology* 9:285-291) have been proposed. These methods are not fit for the mass screening and the cost of performance is expensive. Apart from measuring GAGs, two different approaches have been proposed for MPS detection. One is an immune-capture method for detecting each deficient lysosomal protein from patients with MPS I, MPS II, MPS IIIA and MPS VI (Parkinson-Lawrence et al. (2006), *Clin Chem.* 52:1660-1668; Tan et al. (2008), *Clin Chem* 54:1925-1927) and the other is a direct method, assaying individual enzyme activities for MPS I, MPS II, MPS IIIB, MPS IVA, MPS VI and MPS VII patients (Wang et al. (2005), *Clin Chem* 51:898-900; Gelb et al. (2006), *J Inherit Metab Dis* 29:397-404; Civallero et al. (2006), *Clin Chim Acta* 372:98-102; Wang et al. (2007), *Clin Chem* 53:137-140; Blanchard et al. (2008), *Clin Chem* 54:2067-2070; Chamoles et al. (2002), *Clin Chim Acta* 318:133-137; Duffey et al. (2010), *Bioorg Med Chem Lett* 20:5994-5996; Turecek et al. (2007), *Methods Mol Biol* 359:143-157; Li et al. (2004), *Clin Chem* 50:1785-1796). These approaches, which rely on individual antibodies or enzyme activities for first-tier screening, are still being developed to detect all types of MPS, but will be laborious. It may not be feasible to assay simultaneously all corresponding enzyme or protein levels on a large scale. The utility of these methods for screening is limited by the complicated pretreatment steps required prior to performing mass spectrometry, and a different procedure could be required for each metabolite analyzed.

Chondroitin 6-Sulfate (C6S)

CS is involved in specific biological functions including cell adhesion, morphogenesis, neural network formation, and cell division (Sugahara et al. (2003), *Curr Opin Struct Biol* 13:612-620). Historically, CS was divided into three major subtypes, chondroitin A (chondroitin 4-sulfate; C4S), chondroitin B (dermatan sulfate; DS), and chondroitin C (chondroitin 6-sulfate; C6S), although chondroitin B is not classified as CS any longer. C6S is distributed in the growth plates, especially from the proliferative zone to the hypertrophic zone (Ling et al. (1996) *Avian Dis* 40:88-98), aorta (Yasuda et al. (2013) *Mol Genet Metab* 109:301-311), and cornea (Zhang (2005) *Invest Ophthalmol Vis Sci* 46:1604-1614) in physiological status. C6S has been implicated in pathological status: (1) arterial retention of cholesterol-rich, atherogenic lipoproteins (Mourão et al. (1981) *Biochim Biophys Acta* 674:178-187), a key event that initiates atherosclerosis (Williams and Tabas (1995) *Arterioscler Thromb Vasc Biol* 15:551-561); (2) the connective tissue stroma of human colon carcinomas with increase of C6S (Adany (1990) *J Biol Chem* 265:11389-11396); and (3) urinary excretion of excessive C6S in MPS IVA and VII (Hopwood and Harrison (1982) *Anal Biochem* 119:120-127; Hata and Nagai (1972) *Anal Biochem* 45:462-468; (Haskins et al. (1984) *Pediatr Res* 18:980-984.

To date, CS levels have been determined by HPLC, LC-MS/MS, and capillary electrophoresis, based on the differences in enzymatic digestion using chondroitinase ABC and/or chondroitinase ACII (Imanari et al. (1996), *J Chromatogr A* 720:275-293; Koshiishi et al. (1998), *Anal*

Biochem 265:49-54; Oguma et al. (2001), *Biomed Chromatogr* 15:356-362; Karamanous and Hjerpe (2001), *Methods Mol Biol* 171:181-192; Lamari et al. (2002), *Biomed Chromatogr* 16:95-102). Although capillary electrophoresis studies showed that a CS spot was visualized subjectively in urine of MPS IVA (Hopwood and Harrison (1982), *Anal Biochem* 119:120-127; Hata and Nagai (1972), *Anal Biochem* 45:462-468) C4S and C6S were not separated.

The physiological and pathological roles and distributions of C6S have not been well investigated because of the lack of a rapid, accurate and quantitative method for measurement of that molecule. Thus, no quantitative investigation has been reported on C6S levels in patients with MPS IVA and VII.

There is a need for quantitative molecular marker-based methods for screening individuals for MPS, particularly MPS IVA and MPS VII, and treatment of individuals afflicted with those disorders.

SUMMARY OF THE INVENTION

Provided is a method of detecting mucopolysaccharidosis IVA or mucopolysaccharidosis VII, or for monitoring the progress of mucopolysaccharidosis IVA or mucopolysaccharidosis VII, in a human subject, the method comprising:
(a) providing a biological sample containing glycosaminoglycans derived from the subject;
(b) digesting the sample with an enzyme that converts chondroitin 6-sulfate into ΔDi-6S;
(c) detecting the level of ΔDi-6S generated by said enzyme digestion of the sample by liquid chromatography-tandem mass spectroscopy analysis; and
(d) (i) comparing the level of ΔDi-6S generated from the sample to the level of ΔDi-6S in a control, and determining the subject may be afflicted with mucopolysaccharidosis IVA or mucopolysaccharidosis VII if the level of ΔDi-6S generated from the sample is elevated over the control, or
(ii) comparing the level of ΔDi-6S generated from the sample to the level of ΔDi-6S generated by carrying out steps (b) and (c) on a sample from the same subject taken at a later time point, and determining that the subject's mucopolysaccharidosis has progressed if the level of ΔDi-6S generated from the sample taken at the later time point relative to the level generated from a sample taken at an earlier time point is elevated.

In certain embodiments, the sample is blood, plasma, serum, urine or tissue.

In certain embodiments, the enzyme is chondroitinase C or chondroitinase ABC.

In an embodiment, the method is for detecting mucopolysaccharidosis IVA or mucopolysaccharidosis VII, wherein step (d) comprises comparing the level of ΔDi-6S generated from the sample to the level of ΔDi-6S in a control, and determining the subject may be afflicted with mucopolysaccharidosis IVA or mucopolysaccharidosis VII if the level of ΔDi-6S generated from the sample is elevated over the control.

In certain embodiments, the control comprises an age-matched control.

In certain embodiments, the subject is at least about 5 years of age. In some embodiments, the subject is aged from about 5 to about 35 years, from about 5 to about 20 years, from about 5 years to about 15 years, or from about 5 years to about 10 years. In some embodiments, the subject is a newborn.

In some embodiments, the method for detecting mucopolysaccharidosis IVA or mucopolysaccharidosis VII further comprises detecting the level of keratan sulfate in said sample, and comparing the level of keratan sulfate in the sample to the level of keratan sulfate in a control, and determining the subject may be afflicted with mucopolysaccharidosis IVA if both the level of ΔDi-6S generated from the sample is elevated over its control, and the level of keratan sulfate in said sample is elevated over its control. In some embodiments, the keratan sulfate control and the ΔDi-6S control are from age-matched control subjects. In some embodiments, each control is from the same control subject.

In some embodiments, the method for detecting mucopolysaccharidosis IVA or mucopolysaccharidosis VII further comprises digesting the sample with an enzyme that converts keratan sulfate into Galβ1→4GlcNAc(6S), and comparing the level of said Galβ1→4GlcNAc(6S) generated from the sample to the level of Galβ1→4GlcNAc(6S) in a control, and determining that the subject may be afflicted with mucopolysaccharidosis IVA if both the level of ΔDi-6S generated from the sample is elevated over its control, and the level of Galβ1→4GlcNAc(6S) in said sample is elevated over its control. In some embodiments, the enzyme that converts keratan sulfate into Galβ1→4GlcNAc(6S) is keratanase II. In some embodiments, the Galβ1→4GlcNAc(6S) control and the ΔDi-6S control are from age-matched control subjects. In some embodiments, each control is from the same control subject.

In some embodiments of the method for detecting mucopolysaccharidosis IVA or mucopolysaccharidosis VII, a determination of affliction with mucopolysaccharidosis IVA is confirmed by an N-acetylgalactosamine-6-sulfate sulfatase activity assay.

In some embodiments of the method for detecting mucopolysaccharidosis IVA or mucopolysaccharidosis VII, a determination of affliction with mucopolysaccharidosis IVA is confirmed by a genetic test for a mutation in the gene for N-acetylgalactosamine-6-sulfate sulfatase.

In some embodiments of the method for detecting mucopolysaccharidosis IVA or mucopolysaccharidosis VII, a determination of affliction with mucopolysaccharidosis VII is confirmed by a β-D-glucuronidase activity assay.

In some embodiments of the method for detecting mucopolysaccharidosis IVA or mucopolysaccharidosis VII, a determination of affliction with mucopolysaccharidosis VII is confirmed by a genetic test for a mutation in the gene for β-D-glucuronidase.

In some embodiments, the method for detecting mucopolysaccharidosis IVA or mucopolysaccharidosis VII further comprises treating the subject for said mucopolysaccharidosis IVA or mucopolysaccharidosis VII. In some embodiments, the treatment comprises enzyme replacement therapy. In other embodiments, the treatment comprises hematopoietic stem cell transplantation.

In an embodiment, the method is for monitoring the progress of mucopolysaccharidosis IVA or mucopolysaccharidosis VII, wherein step (d) comprises comparing the level of ΔDi-6S generated by carrying out steps (b) and (c) on a sample from the same subject taken at a later time point, and determining that the subject's mucopolysaccharidosis has progressed if the level of ΔDi-6S generated from the sample taken at the later time point relative to the level generated from a sample taken at an earlier time point is elevated.

In some embodiments of the aforesaid monitoring method, the method further comprises detecting the level of keratan sulfate in said sample, and comparing the level of keratan sulfate in the sample to the level of keratan sulfate from a sample taken from the subject at a later time point, and determining the subject's mucopolysaccharidosis has progressed if both the level of ΔDi-6S and the level of keratan sulfate are elevated at the later time point relative to the levels at the earlier time point.

In some embodiments of the aforesaid monitoring method, the method further comprises digesting the sample with an enzyme that converts keratan sulfate into Galβ1→4GlcNAc(6S), and comparing the level of said Galβ1→4GlcNAc(6S) generated from the sample to the level of Galβ1→4GlcNAc(6S) generated from a sample from the same subject taken at a later time point, and determining the subject's mucopolysaccharidosis has progressed if both the level of ΔDi-6S and the level of Galβ→4GlcNAc(6S) are elevated at the later time point relative to the levels at the earlier time point.

Also provided is a method for monitoring the efficacy of a treatment of mucopolysaccharidosis IVA or mucopolysaccharidosis VII in a human subject. The method comprises:
(a) providing a biological sample containing glycosaminoglycans derived from the subject at a time point during or after a course of therapy for said mucopolysaccharidosis IVA or mucopolysaccharidosis VII;
(b) digesting the sample with an enzyme that converts chondroitin 6-sulfate into ΔDi-6S;
(c) detecting the level of ΔDi-6S generated by said enzyme digestion of the sample by liquid chromatography-tandem mass spectroscopy analysis; and
(d) comparing the level of ΔDi-6S generated from the sample to the level of ΔDi-6S generated by carrying out steps (b) and (c) on a sample taken from the subject at an earlier time point before or during the course of therapy, and determining that the course of therapy is not likely efficacious in treating said mucopolysaccharidosis if the level of ΔDi-6S generated from the sample taken at the later time point is elevated in comparison to the level of ΔDi-6S generated from the sample taken at the earlier time point.

In some embodiments of the aforesaid method for monitoring therapy efficacy, the method further comprises detecting the level of keratan sulfate in said sample, and comparing the level of keratan sulfate in the sample to the level of keratan sulfate from the sample taken from the subject at the earlier time point, and determining that the course of therapy is not likely efficacious in treating said mucopolysaccharidosis if both the level of ΔDi-6S and the level of keratan sulfate are elevated at the later time point relative to the levels at the earlier time point.

In some embodiments of the aforesaid method for monitoring therapy efficacy, the method further comprises digesting the sample with an enzyme that converts keratan sulfate into Galβ1→4GlcNAc(6S), and comparing the level of said Galβ1→4GlcNAc(6S) generated from the sample to the level of Galβ1→4GlcNAc(6S) generated from a sample from the same subject taken at the earlier time point, and determining that the course of therapy is not likely efficacious in treating said mucopolysaccharidosis if both the level of ΔDi-6S and the level of Galβ1→4GlcNAc(6S) are elevated at the later time point relative to the levels at the earlier time point.

In some embodiments, the monitored therapy comprises enzyme replacement therapy. In other embodiments, the monitored therapy comprises hematopoietic stem cell transplantation.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

ABBREVIATIONS AND DEFINITIONS

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

By ΔDi-6S is meant 2-acetamido-2-deoxy-4-O-(4-deoxy-α-L-threo-hex-4-enopyranosyluronic acid)-6-O-sulfo-D-glucose.

By ΔDi-4S is meant 2-acetamido-2-deoxy-4-O-(4-deoxy-α-L-threo-hex-4-enopyranosyluronic acid)-4-O-sulfo-D-glucose.

By "control" or "control sample" is meant a sample from a subject that does not suffer from a mucopolysaccharidosis. A "control" can also refer to a value or range of values derived from analysis of pooled control samples.

By "liquid chromatography-tandem mass spectroscopy analysis" or "LC-MS/MS" is meant a chemical analytical technique that combines liquid chromatography with tandem mass spectrometry for quantification of substances in a mixture of substances. By "tandem mass spectrometry", also known as "MS/MS", is meant a multi-step mass spectrometry technique using a separate mass spectroscope for each step or by using the same spectroscope to perform steps sequentially, typically with some form of fragmentation occurring in between the steps.

By "sample" or "test sample" as used herein means a biological material isolated from an individual. The test sample may contain any biological material suitable for detecting the desired biomarkers.

DETAILED DESCRIPTION OF THE INVENTION

According to the present invention, a rapid detection method for the presence of MPS IVA or MPS VII is provided, based upon a robust procedure that detects and discriminates C6S from C4S from in human subject samples. The discrimination of C6S from C4S has unexpectedly revealed C6S as a novel and independent biomarker of MPS IVA/VII. C6S is detected and quantified in patient samples through digestion with an enzyme that converts CS into its disaccharide ΔDi-6S. ΔDi-6S is discriminated from disaccharides derived from degradation of other GAGs (DS and C4S) by liquid chromatography-tandem mass spectroscopy analysis. Thus, the method for quantifying C6S can be utilized as part of a multiplex assay procedure where multiple GAGs (KS, HS, CS and DS) are quantified.

The biomarker method for the detection of MPS IVA and MPS VII may be utilized to rapidly screen individuals for likely affliction by MPS IVA and MPS VII; to serve as a confirmatory diagnosis tool in conjunction with other diagnostic methods for detecting MPS IVA and/or MPS VII; to assess the disease severity or disease progression in MPS IVA and MPS VII patients; to monitor therapeutic efficacy during treatment, based upon C6S level in subject specimens. In particular, the test for C6S is conveniently carried out on blood-based samples, such as blood, (e.g. fresh or dried blood spot), plasma and serum.

Figure 1:
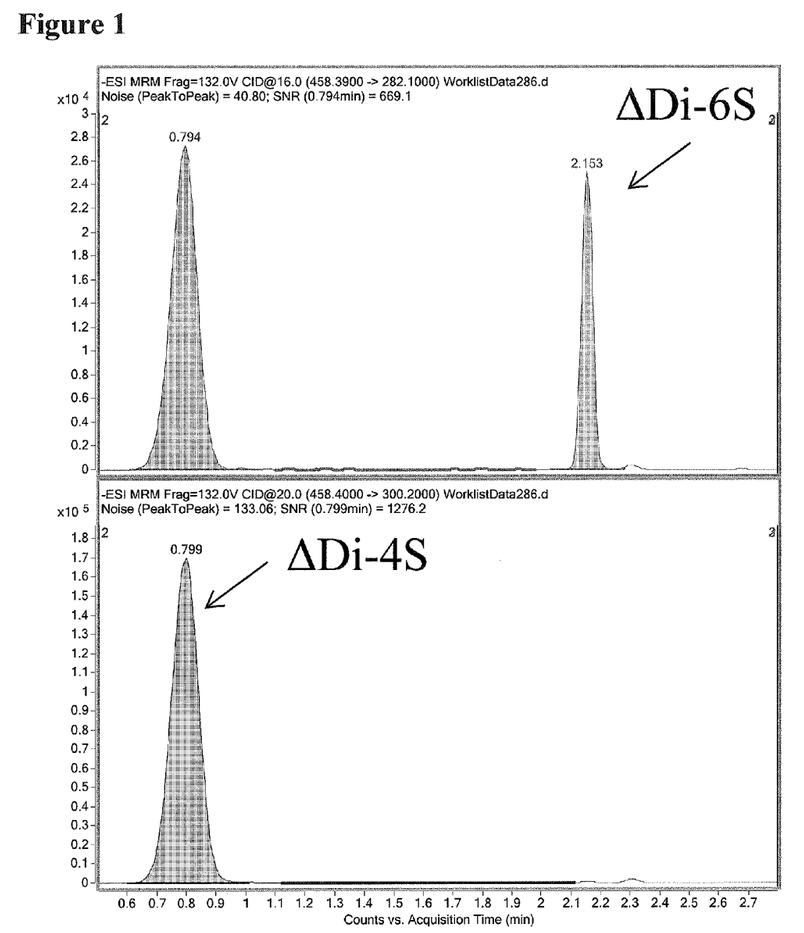
FIG. 1 shows representative ΔDi-4S and ΔDi-6S Multiple-Reaction Monitoring chromatograms of extracts obtained from a patient with MPS IVA.

Prior GAG analytical methods relying on sample enzyme digestion and LLC-MS/MS analysis of disaccharides have failed to resolve a peak corresponding to a mixture of disaccharides derived from digestion of C6S, C4S and DS. See U.S. Pub. No. 2011/0008810, FIGS. 3A and 3B. According to the present method, LC-MS/MS peaks corresponding to ΔDi-6S (derived from C6S) and Di-4S (derived from DS and C4S) are separated by the LC component of the LC-MS/MS analysis. Under conditions reported in the Examples that follow, ΔDi-6S and ΔDi-4S were characterized by LC retention times of 2.15 and 0.83 minutes, respectively, thus providing a robust separation, thereby permitting for the first time quantification of ΔDi-6S, and thus quantification of C6S.

Subject biological samples are collected for analysis from, for example, body fluids such as blood, plasma, serum, urine, or other bodily fluids. In other embodiments, the sample comprises tissue. No particular limitation is placed on the nature of the sample so long as it contains mucopolysaccharides. In one embodiment, a blood sample may be in dried form, e.g., blood spot.

The sample may be subjected to filtration, including ultrafiltration, to concentrate mucopolysaccharides for analysis. No particular limitation is imposed on the filtration method and apparatus employed, so long as the filter does not allow mucopolysaccharides to pass there through, but allows passage of molecules smaller than mucopolysaccharides in molecular weight. In one embodiment the filter media is a 10K filter, e.g., Ultrafiltration Omega 10K membrane filter (PAL Life Sciences, NY,). The membrane filters may be conveniently deployed in multiples format using, e.g., a multi-well plate, (e.g., an AcroPrep™ 96-Well Filter Plate (PALL Life Sciences), to permit simultaneous processing of multiple samples. The filter plate may be optionally subjected to centrifugation, e.g., at 2,000×g for 15 minutes.

The filtered sample is then digested with one or more enzymes that converts C6S in the sample to ΔDi-6S. The digesting enzyme may comprise, for example, chondroitinase C or chondroitinase ABC. Chondroitinase ABC catalyzes the eliminative degradation of polysaccharides containing (1-4)-β-D-hexosaminyl and (1-3)-β-D-glucuronosyl or (1-3)-α-L-iduronosyl linkages to disaccharides containing 4-deoxy-β-D-gluc-4-enuronosyl groups. It acts on C4S, C6S, and DS, and acts slowly on hyaluronate Enzymatic digestion may be carried out, for example, over a period of 1-30-hour digestion at about 30 to 40° C. Preferably, enzymatic digestion is performed in a 37° C. incubator for 15 hours. The digestion product is optionally and preferably centrifuged for subsequent LC-MS/MS analysis Centrifugation is performed, for example, at 2,000×g for 15 minutes.

The present method for quantifying C6S may be utilized as part of a multiplex assay procedure where multiple GAGs (KS, HS, CS and DS) are quantified. The appropriate mixture of GAG-specific enzymes are utilized in combination or separately. Other GAG-degrading enzymes for producing GAG degradation products include, for example, keratanase, keratanase II, heparitinase, heparitinase I, heparitinase II.

In one embodiment, KS in the patient subject is detected and quantified along with CS6. Thus, enzymatic digestion is carried out with a mixture of a CS-specific enzyme and a KS specific enzyme. The KS-specific enzyme may comprise, for example, keratanase, preferably keratanase II. The multi-enzyme digestion may be carried out under the same conditions as for digestions utilizing CS-specific enzyme.

The enzyme-digestion product is analyzed by an LC-MS/MS procedure. LC-MS/MS analysis of GAG-degradation products is described, for example, in U.S. Pub. No. 2011/0008810. In the typical an LC-MS/MS procedure, a liquid chromatography (LC) component separates sample components and then introduces them to a mass spectrometer (MS). The MS creates and detects charged ions. The LC/MS data may be used to provide information about the molecular weight, structure, identity and quantity of specific sample components.

Mass spectrometers operate by converting the analyte molecules to a charged (ionized) state, with subsequent analysis of the ions and any fragment ions that are produced during the ionization process, on the basis of their mass to charge ratio (m/z). A typical LC-MS/MS instrument contains: (i) an atmospheric pressure ionization source, typically an electrospray ionization source or an atmospheric pressure chemical ionization source, coupled by (ii) an ion-inlet and focusing component, which provides both transition from atmospheric pressure to vacuum and ion-focusing, into (iii) a first mass-filtering device, which leads into (iv) a collision chamber that can be filled with low-pressure gas for collision-induced dissociation, followed by (v) a second mass-filtering device, and finally (vi) an ion-impact detector (electron multiplier). The construction, operation and applications of LC-MS/MS instruments is reviewed by Grebe and Singh (2011), *Clin Biochem Rev* 32:5-31.

No particular limitation is imposed on the LC-MS/MS chromatography system, so long as the system can achieve adequate separation of disaccharides. Examples of a chromatography apparatus consists of the combination of a carbon graphite column and a reverse phase HPLC column. Examples of commercially available carbon graphite columns include Hypercarb (2.0 mm i.d.×50 mm, 5 μm) (Thermo Electron Corp). Examples of reverse phase HPLC system include the 1260 Infinity Quaternary LC System (Agilent Technologies, USA).

Representative chromatography conditions include, e.g., a column temperature of 50° C.; a mobile phase gradient elution of 5 mM ammonium acetate in acetonitrile-5 mM ammonium acetate buffer (pH 11.0); and a gradient condition program as follows: (i) initial composition of 0% acetonitrile kept for 0.1 min, linearly modified to 30% over 1.8 min, maintained at 30% for 0.3 min, modified to 0% over 0.01 min, and finally maintained at 0% for 2.5 min; flow rate: 0.7 ml/min.

The mass spectroscopy component of the analysis may be carried out using any appropriate mass spectrometer, e.g., a 6460 Triple Quad mass spectrometer (Agilent Technologies) or equivalent device.

In one embodiment, LC-MS/MS analysis is conducted on a sample treated with a mixture of CS-specific and KS-specific enzymes to digest "polymer" C6S and KS, respectively, to disaccharides for analysis. Mass spectrometry is used to detect ions by monitoring: (i) the decay of the m/z 462 precursor ion to m/z 97 production for Galβ1→4GlcNAc(6S) disaccharides derived from KS; (ii) the decay of the m/z 458.4 precursor ion to the m/z 282.1 product ion for ΔDi-6S (derived from C6S); (iii) the decay of the m/z 458.4 precursor ion to the m/z 300.2 product ion for ΔDi-4S (derived from DS); and (iv) the decay of the m/z 354.29 precursor ion to the m/z 193.1 product ion for an internal standard (chondrosine). Peak areas for all components are integrated automatically by appropriate quantitative analysis software (e.g., QQQ Quantitative Analysis software, Agilent Technologies). Peak area ratios (area of analytes/area of internal standard) are plotted against concentration by weighted linear regression. The levels for each disaccharide are calculated using the quantitative analysis software (e.g., QQQ Quantitative Analysis software).

For detection of MPS IVA/VII, the level of the disaccharide ΔDi-6S (derived from C6S) generated from the subject sample is compared with the level contained in one or more normal control samples processed in the same fashion. Preferably, the control samples comprise aged-matched control samples, to accommodate age-related changes in markers. By "age-matched" is meant samples sourced from normal healthy individuals of approximately the same age as the test subject under study. The age of the control donor is preferably within three years, more preferably within two years, most preferably within one year, of the age of the test subject.

In certain embodiments, the test subject is at least about five years of age. In some embodiments, the subject is aged from about 5 years to about 35 years, from about 5 to about 20 years, from about 5 years to about 15 years, or from about 5 years to about 10 years. In some embodiments, the subject is a newborn.

In one embodiment, MPS IVA is detected by analysis of the levels of both C6S (as its digestion product ΔDi-6S) and KS. The combination of elevated C6S and KS levels is observed to distinguish test subjects patients suffering from MPS IVA from control subjects more clearly compared to the level of C6S alone. The level of KS in the test sample may be determined as above, based on inclusion of a KS-specific enzyme in the enzyme digestion step of sample preparation and quantitating the KS digestion product, i.e., Galβ1→4GlcNAc(6S). The level of Galβ→4GlcNAc(6S) is compared to the level of one or more controls.

Alternatively, the KS level may be determined by other means, such as by colorimetric analysis using dimethylmethylene blue, such as described by Melrose & Ghosh (1988), *Anal Biochem* 170:293-300; or ELISA, as described by Tomatsu et al. (2004), *Pediatr Res* 55:592-597 and Tomatsu et al. (2005), *J Inherit Metab Dis* 28:187-202; or HPLC, as described by Linhardt et al. (1989) *Anal Biochem* 181:288-296 and Whithman et al. (1999), *Glycobiology* 9:285-291.

The KS controls, like the C6S controls employed, are preferably age-matched with the test subject sample. Preferably, both the C6S and KS controls are from the same subject.

The method of the present invention may be utilized in one embodiment as a rapid screen for the likely presence of MPS IVA and VII in subjects. Confirmation of a diagnosis of MPS IVA and VII may be conducted, for example, by an appropriate in vitro enzyme assay (available in either blood or cultured fibroblasts from a skin biopsy). Definitive diagnosis of MPS IVA, may comprise detecting a deficiency in GALNS enzyme activity. GALNS enzyme activity can be measured in cultured fibroblasts or leukocytes. For example a fluorometric enzyme assay for GALNS may be performed using the fluorogenic substrate 4-methylumbelliferyl-β-D-galactose-6-sulfate according to van Diggelen et al., *Clin. Chim. Acta* (1990) 187:131-139. Alternatively, a diagnosis of MPS IVA may be confirmed by molecular genetic testing for the presence of mutations in the gene for GALNS (Tomatsu et al. (2005), *Hum Mutat* 26:500-512; Morrone et al. (2014), *Mol Genet Metab* doi: 10.1016/j.ymgme.2014.03.004).

Definitive diagnosis of MPS VII may be obtained, for example, by an appropriate in vitro enzyme assay of β-D-glucuronidase activity (Speleman et al. (1996), *Cytogenet Cell Genet* 72:53-55). A deficiency in β-D-glucuronidase activity is indicative of MPS VII. Alternatively, a diagnosis of MPS VII may be confirmed by molecular genetic testing for the presence of mutations in the gene for β-D-glucuronidase (Tomatsu et al. (2009), *Hum Mutat* 30:511-519; Hytönen et al. (2012), *PLoS One* 7:e40281).

Moreover, after a specific diagnosis has been established, the method of the invention may be utilized for monitoring the progress of mucopolysaccharidosis IVA or mucopolysaccharidosis VII in the patient. The C6S-specific assay method described above, based on detection and quantification of the level of ΔDi-6S, may be carried out on a sample from the same subject taken at a later time point. The subject's mucopolysaccharidosis is deemed to have progressed form the initial determination if the level of ΔDi-6S generated from the later time sample relative to the level generated from an earlier sample is elevated. The KS level is optionally and preferably assayed also, at both time points. Increase in the level of both markers over time serves as further confirmation of further progress of mucopolysaccharidosis.

In another embodiment, the assay method may be utilized to monitor the effectiveness of treatment, such as a bone marrow transplant, enzyme replacement therapy, or other therapy. The C6S-specific assay method described above, based on detection and quantification of the level of ΔDi-6S, may be carried out on a sample from the same subject taken at a time point during or after a course of mucopolysaccharidosis therapy. A continued increase in the patient's C6S level over an earlier pre-therapy determination indicates that the disease is progressing and that the therapy is likely not to be efficacious. The KS level is optionally and preferably assayed also, at both time points. Increase in the level of both markers over time serves as further confirmation of further progress of mucopolysaccharidosis, and that the therapy is likely not efficacious.

In other embodiments, a subject that is determined by the above assay method to likely suffer from mucopolysaccharidosis IVA or mucopolysaccharidosis VII is then treated.

Treatment for MPS IVA or MPS VII may constitute introduction of functional enzyme to augment the function of the subject's genetically defective enzyme, i.e., GALNS in the case of MPS IVA, and β-glucuronidase in the case of MPS VII. Treatment for either condition comprises administering to the subject a therapeutically effective amount of the functional replacement enzyme. The introduced enzyme is taken up by the lysosomes of the subject, thereby increasing GAG catabolism. Introduction of enzyme can comprise supplying the replacement enzyme exogenously as "enzyme replacement therapy" (ERT), or endogenously by means of hematopoietic stem cell transplantation (HSCT). In the latter, replacement enzyme is supplied endogenously through synthesis by the transplanted stem cells.

Protocols for ERT for treatment of mucopolysaccharidosis are known. ERT generally involves i.v. infusions of the recombinant human enzyme weekly or every other week. Products are administered intravenously either through a peripheral line or central access device, such as a Port-a-Cath. Each infusion is given for 1-6 hours depending on the enzyme, the dose, and the patient's previous adverse event history. The patient is closely monitored for infusion reactions.

In one embodiment, treatment for MPS IVA comprising administering to the subject a therapeutically effective amount of GALNS. The GALNS may comprise, for example, VIMIZIM™ brand GALNS (elosulfase alfa, BioMarin Pharmaceutical Inc.), administered according to the manufacturer's prescribing information (1 mg/ml injection given in a recommended dosage of 2 mg per kg body weight and administered once every week as an intravenous infusion over a minimum of 3.5 to 4.5 hours, based on infusion volume). For a further discussion of GALNS enzyme replacement therapy for MPS IVA see, for example, US Pat. Pub. 2012/0189605.

For HSCT, stem cell sources for transplantation include bone marrow and umbilical cord blood. The latter requires a less strict HLA matching than bone marrow transplantation. HSCT typically involves a toxic ablative conditioning regimen to eliminate the patient's own stem cell population, followed by immunosuppression and semi-isolation for up to 12 months. MPS VII has been successfully treated with allogeneic bone marrow therapy. See Yamada et al., *Bone Marrow Transplantation* (1998), 21:629-634. (3.18 3 108/kg bone marrow total nucleated cells from an unrelated female donor matched in blood type, HLA-A, B, DR, DQ, and DP, after conditioning with busulfan (4 mg/kg/day 3 4 days), cyclophosphamide (50 mg/kg/day 3 4 days) and rabbit anti-human thymocyte globulin (3.75 mg/kg/day 3 4 days).

Therapy for MPS-IVA and MPS VII may also take the form of substrate reduction therapy (SRT) SRT aims to decrease the amount of stored material through the administration (usually oral) of small molecules that are capable of inhibiting the synthesis of the substrate stored in that specific disease, resulting in the restoration of the balance between synthesis and degradation. SRT may comprise administration of a therapeutically effective amount of an inhibitor of glucosylceramide synthesis, or agent capable of increasing the rate of neuronal glycolipid degradation. See, for example, WO 12/055064, describing such therapies. Such inhibitors and agents may comprise, for example, small molecules and peptides. Small molecules include, for example, N-butyldeoxynojirimycin, N-butyldeoxygalactonojirimycin, and other imino sugar-structured inhibitors of glucosylceramide synthesis. Other small molecule inhibitors of glycosylceramide synthesis include agents such as 1-phenyl-2-decanoylamino-3-morpholino-1-propanol (PDMP), D-threo-1-phenyl-2-decanoylamino-3-morpholino-1-propanol and structurally related analogues thereof. 5,7-Dihydroxy-3-(4-hydroxyphenyl)-4H-1-benzopiran-4-one, also known as genistein or 4,5,7-trihydroxyisoflavone, has been demonstrated to be an inhibitor of GAGs synthesis.

The practice of the invention is illustrated by the following non-limiting example. The studies that follow demonstrate that C6S levels in patients with MPS IVA and VII are significantly higher than that in age-matched control subjects. Over 93% of patients with MPS IVA showed elevation of either C6S or KS level above +2 SD of age-matched control subjects, although C6S or KS level alone showed that around 75% patients have above +2 SD of the level in age-matched control subjects. This suggests that the combination of C6S and KS levels may distinguish patients with MPS IVA and control subjects more clearly compared with either C6S alone.

EXAMPLE

The level of C6S and KS in the blood of control subjects and patients with MPS IV or MPS VII was measured by LC-MS/MS after digestion of GAGs in the blood by chondroitinase ABC and keratanase II.

Subjects

Blood (plasma or serum) samples were obtained from 35 patients with MPS IVA (phenotype: severe; 32, undefined; 3), 4 patients with MPS IVB (phenotype: attenuated; 4), and 3 patients with MPS VII after informed consent had been obtained from each patient. For all samples, the ages of the patients were identified. Blood samples were also obtained from 138 healthy controls. In previous experiments by LC-MS/MS, we confirmed that there is no difference of GAG value in specificity and sensitivity between plasma and serum (Tomatsu et al., (2010) *Mol Genet Metab* 99:124-131; Tomatsu et al., (2010) *J Inherit Metab Dis* 33:141-150; Tomatsu et al., (2010) *Inherit Metab Dis* 33:S35-42).

The diagnosis of MPS IVA, MPS IVB, and MPS VII in the patients was made on the basis of reduced enzyme activity (GALNS, β-galactosidase, and β-D-glucuronidase, respectively) of ≤5% the normal level in plasma, leukocytes or fibroblasts. Clinical severity for patients with MPS IVA was classified based on growth charts, as previously described (Montaño et al. (2008), *Am J Med Genet A* 146A:1286-1295; Tomatsu et al. (2012), *J Inherit Metab Dis* 33:141-150). According to the isopleth upon which the patient fell, patients above the 90th percentile on the growth chart for each gender were defined as attenuated (Tomatsu et al. (2012), *J Inherit Metab Dis* 33:141-150). The severity of the disease in patients with MPS IVB was also classified compared with growth charts of MPS IVA, since the growth chart of MPS IVB was not available.

Materials

Chondroitinase ABC and keratanase II were obtained from Seikagaku Co (Tokyo, Japan) for the digestion of polymer C6S and KS to disaccharides. Chondroitinase A produces disaccharides of C4S, while chondroitinase B and chondroitinase C produce disaccharides of DS and C6S, respectively. All disaccharides had the same molecular mass. C6S was separated from DS and C4S as detailed below.

Chondrosine for internal standard (IS), ΔDi-6S (C6S) [2-acetamido-2-deoxy-4-O-(4-deoxy-a-L-threo-hex-4-enopyranosyluronic acid)-6-O-sulfo-D-glucose], and ΔDi-4S (DS) [2-acetamido-2-deoxy-4-O-(4-deoxya-L-threo-hex-4-enopyranosyluronic acid)-4-O-sulfo-D-glucose] were provided from Seikagaku Co. Stock solutions of ΔDi-6S (100 μg/ml), ΔDi-4S (100 μg/ml), "polymer" KS (20 μg/ml), and IS (5 mg/ml) were prepared separately in ddH$_2$O. Standard solutions of ΔDi-6S (10, 20, 100, 200, and 1000 ng/ml), KS (0.1, 0.2, 1.0, 2.0 and 10.0 μg/ml), and IS solution (500 ng/ml) were freshly prepared.

Sample Preparation

Blood specimens and standards were prepared as follows. Ten μL of each serum or plasma sample and 90 μL, of 50 mM Tris-hydrochloric acid buffer (pH 7.0) were placed in wells of AcroPrep™ Advance 96-Well Filter Plates that have Ultrafiltration Omega 10K membrane filters (PALL corporation, NY, USA). The filter plates were placed on a receiver and centrifuged at 2,000 g for 15 min to remove free disaccharides. The membrane plates were transferred to a fresh receiver plate. Standards were added to unused wells of the filter plate. 20 µL, of IS solution (500 ng/ml), 60 µL of 50 mM Tris-hydrochloric acid buffer (pH 7.0), and 10 µL of the chondroitinase ABC and keratanase II mixture solution (2 mU each per sample) were added to each filter well. The plates were incubated in a water bath at 37° C. for 15 hr and centrifuged at 2000 g for 15 min. The receiver plate containing disaccharides was stored at −20° C. until LC-MS/MS injection.

Apparatus

The chromatographic system consisted of a 1260 Infinity Binary Liquid Chromatography System (Agilent Technologies, Palo Alto, Calif., USA) and a Hypercarb™ Column (2.0 mm i.d. 50 mm, 5 µm, Thermo Electron, USA). The column temperature was kept at 50° C. The mobile phase was a gradient elution of 5 mM ammonium acetate in acetonitrile-5 mM ammonium acetate buffer (pH 11.0). The initial gradient condition was programmed as follows. The initial composition of 0% acetonitrile was kept for 0.1 min, linearly modified to 30% over 1.8 min, maintained at 30% for 0.3 min, modified to 0% over 0.01 min, and finally maintained at 0% for 2.5 min. The flow rate was 0.7 ml/min. A 6460 Triple Quad mass spectrometer (Agilent Technologies) was operated in the negative ion detection mode. In the multiple reaction monitoring (MRM) mode, the mass spectrometer was used to detect ions by monitoring the decay of the m/z 462 precursor ion to m/z 97 production for Galβ1→4GlcNAc(6S) disaccharides derived from KS, the decay of the m/z 458.4 precursor ion to the m/z 282.1 product ion for ΔDi-6S (C6S), the decay of the m/z 458.4 precursor ion to the m/z 300.2 product ion for ΔDi-4S (DS), and the decay of the m/z 354.29 precursor ion to the m/z 193.1 product ion for IS. Peak areas for all components were integrated automatically by using QQQ Quantitative Analysis software (Agilent Technologies). Peak area ratios (area of analytes/area of IS) were plotted against concentration by weighted linear regression. Raw LC-MS/MS data were automatically preserved. The levels for each disaccharide were calculated using QQQ Quantitative Analysis software.

Method Validation

Intra-day precision evaluated as coefficient of variation (CV) was determined by replicate analyses (n=5) of three different control sera. Inter-day precision was determined by replicate analyses (n=5) of three different serum controls on 3 separate days. The selectivity of the assay was investigated by processing and analyzing five independent samples by the procedure described above without enzymatic digestion. Calibration curves were constructed by plotting the peak area ratio of the analytes to IS against the concentration of the analytes. Each calibration curve consisted of seven calibration points (n=1).

Statistical Analysis

Statistical analysis was performed using SPSS for Windows (version 17.0, SPSS Inc., Chicago, Ill., USA). For age-match comparisons, patient and control samples were grouped in age ranges <3, 3-4, 5-9, 10-14, 15-35 and 36+. Data were shown as the mean±SD.

Results

LS-MS/MS Conditions

The peaks of ΔDi-6S (C6S) and ΔDi-4S (DS and C4S) with the same molecular weight were separated by the LC component of the system (FIG. 1). The retention time of ΔDi-6S and ΔDi-4S were 2.15 and 0.83 min, respectively.

Calibration Curves

Calibration curves for ΔDi-6S and Galβ1→4GlcNAc(6S) (KS) obtained on 5 separate days were linear over the concentration ranges of 10 to 1000 ng/ml and 0.1 to 10 µg/ml, respectively. The correlation coefficients of determination (r) were not less than 0.99.

Precision and Accuracy

Results of intra- and inter-assay precision for ΔDi-6S and Galβ1→4GlcNAc(6S) in control specimens are as follows. The intra-assay precision values/coefficient of variation (CV) determined from analysis of ΔDi-6S and Galβ1→4GlcNAc(6S) for control serum were less than 11.9 and 6.8%, respectively. The inter-assay precision values/CVs for these disaccharides in control serum were less than 12.2, and 6.5%, respectively. These results demonstrate the reproducibility and accuracy of the method.

Chondroitin-6-Sulfate (C6S) Level

Figure 2:
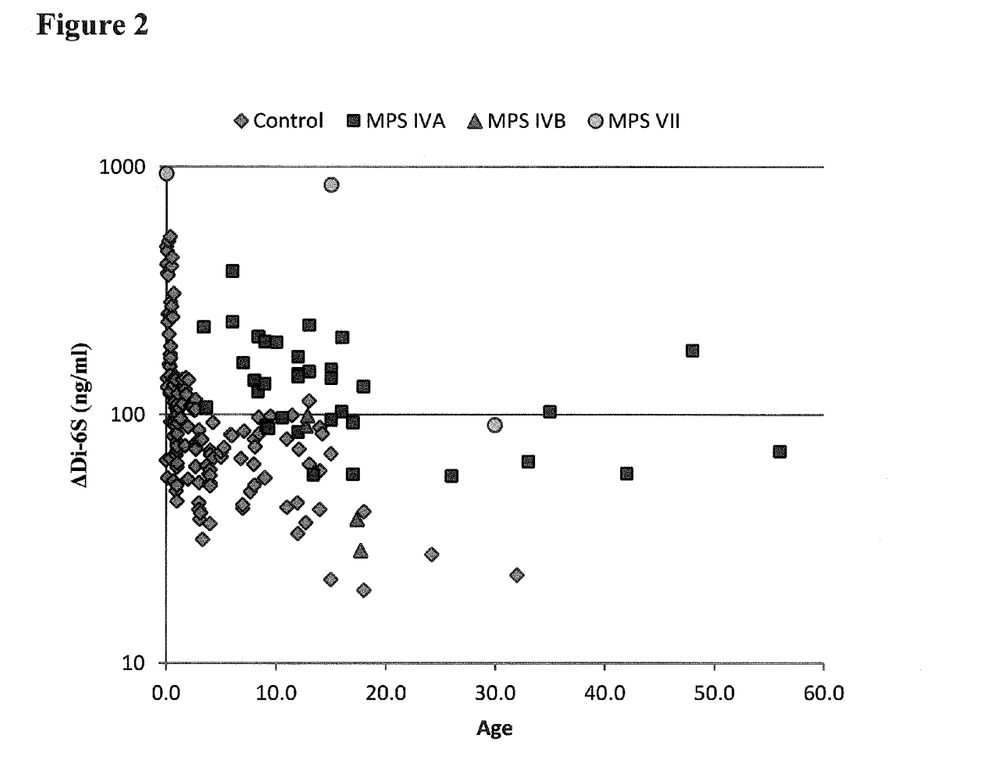
FIG. 2 shows levels of ΔDi-6S in blood of patients with MPS and in blood of control subjects.

The C6S values for the blood samples from 35 MPS IVA patients (average age: 16.1 years, range 3.4-56 years), 4 MPS IVB patients (average age: 15.2 years, range 12.7-17.7 years), 3 MPS VII patients (average age: 15 years, range 0-30 years), and 138 control subjects (average age 4.1 years; range 0-32 years) are described in Table 1 and FIG. 2. Blood C6S levels in control subjects were found to vary with age. The level was the highest in newborns and rapidly decreased until 5 years of age. After 5 years of age, there was a gradual decline with age. Blood C6S concentrations in patients with MPS IVA also showed age-dependency. The C6S levels in samples from patients with MPS IVA in age groups 5-9 years, 10-14 years, and 15-35 years were significantly higher than those in age-matched controls ($p<0.001$, $p<0.001$, and $p<0.005$, respectively). Only 2 MPS IVA patients were younger than 5 years old, so although levels of C6S were high in these patients, significance could not be determined (Table 1, FIG. 2).

C6S was also found to be elevated in urine of patients with MPS IV and VII (data not shown).

The level of C6S was also compared between patients with MPS IVB and VII and the age-matched controls (Table 1, FIG. 2). Four patients with MPS IVB showed that the level of C6S was within those seen of age-matched controls (FIG. 2). Blood C6S levels in all three patients with MPS VII were above the mean 2 SD above the mean age-matched controls (Tables 1, 3).

Keratan Sulfate (KS) Level

Figure 3:
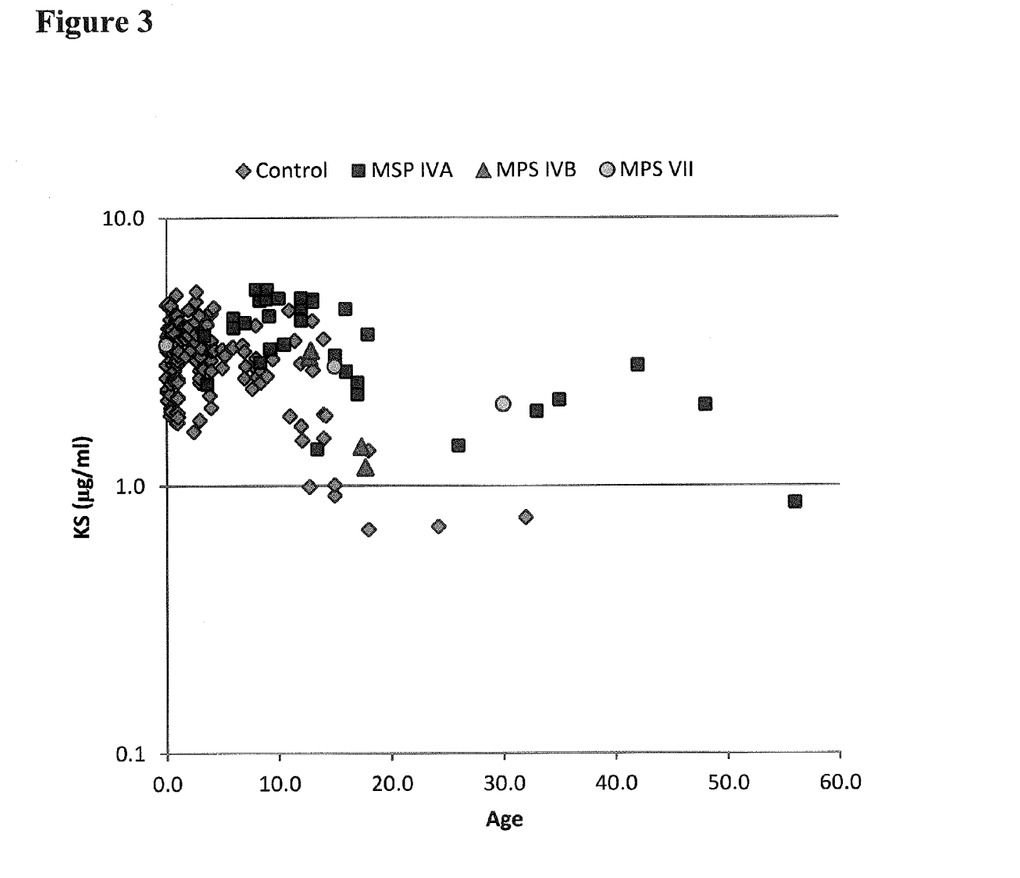
FIG. 3 shows levels of blood KS of patients with MPS and control subjects. Results of all specimens from patients and control subjects were plotted on a semilogarithmic scale with respect to age (years).

KS levels in blood samples from the same patients with MPS IVA, IVB, and VII and the same control subjects in C6S assay are shown in Table 2 and FIG. 3. Blood KS levels in control subjects were also age-dependent. Blood KS levels were highest in children up to 10 years of age and then gradually declined in older children and adults. As seen for C6S, KS in blood of patients with MPS IVA in age groups between 5-9 years, 10-14 years, and 15-35 years were significantly higher than those in age-matched control subjects ($p<0.001$, $p<0.005$, and $p<0.001$, respectively) (Table 2, FIG. 3). KS levels in blood from two MPS IVA patients younger than 5 were indistinguishable from controls and there was significant overlap of KS values between control subjects and patients with MPS IVA in the entire age range (FIG. 3).

The levels of KS were also compared between patients with MPS IVB and VII and the age-matched controls (Table 2, FIG. 3). All samples in patients with MPS IVB showed that blood KS level was within the level of the age-matched controls (Table 2). Blood KS values for two younger patients with MPS VII were more than 2 SD above the mean of the age-matched controls (Tables 2, 3).

Correlation Between KS and C6S Levels

Correlation between KS and C6S levels was not observed (r2=0.1136). For C6S, 75% (24 out of 32) of the patients with MPS IVA were more than 2 SD above the mean of age-matched controls. For KS this proportion was 71.9% (23 out of 32). For either C6S or KS, 29 out of 32 (90.6%) patients were more than 2 SD above the mean for either C6S or KS level in the age-matched control subject (Table 3). The combined data of C6S and KS provided more difference between controls and patients with MPS IVA, compared with C6S or KS by alone.

TABLE 1

Levels of C6S in patients with MPS IVA, IVB, and VII

| ΔDi-6S (ng/ml) | Control | MPS IVA | MPS IVB | MPS VII |
|---|---|---|---|---|
| <3 | 156.7 ± 116.9 (n = 81) | | | 940.7 (n = 1) |
| 3-4 | 58.7 ± 17.4 (n = 20) | 166.4 ± 83.8 (n = 2) | | |
| 5-9 | 70.5 ± 17.1 (n = 18) | 175.7 ± 87.2 *** (n = 12) | | |
| 10-14 | 66.1 ± 25.9 (n = 13) | 141.7 ± 54.9 *** (n = 8) | 94.9 ± 6.2 (n = 2) | |
| 15-35 | 33.6 ± 19.2 (n = 6) | 109.2 ± 45.0 ** (n = 11) | 33.2 ± 6.8 (n = 2) | 468.2 ± 533.8 (n = 2) |
| >36 | | 103.7 ± 68.0 (n = 3) | | |

Data represent the mean ± SD values.
*, , *; Significantly different from the control at p < 0.05, 0.005 and 0.001.

TABLE 2

Levels of KS in patients with MPS IVA, IVB, and VII

| KS (μg/ml) | Control | MPS IVA | MPS IVB | MPS VII |
|---|---|---|---|---|
| <3 | 3.2 ± 0.9 (n = 81) | | | 3.4 (n = 1) |
| 3-4 | 3.2 ± 0.9 (n = 20) | 3.0 ± 0.9 (n = 2) | | |
| 5-9 | 2.9 ± 0.4 (n = 18) | 4.3 ± 0.9 *** (n = 12) | | |
| 10-14 | 2.5 ± 1.1 (n = 13) | 4.2 ± 1.2 ** (n = 8) | 3.1 ± 0.1 (n = 2) | |
| 15-35 | 0.9 ± 0.3 (n = 6) | 2.7 ± 0.9 *** (n = 11) | 1.3 ± 0.2 (n = 2) | 2.4 ± 0.5 (n = 2) |
| >36 | | 1.9 ± 1.0 (n = 3) | | |

Data represent the mean ± SD values.
*, , and *; significantly different from the control at p < 0.05, 0.005, and 0.001, significantly.

TABLE 3

Ratio of 2 SD above the mean of the age-matched controls in MPS IVA, IVB, and VII

| | C6S | KS | Either C6S or KS |
|---|---|---|---|
| MPS IVA | 75% (24 out of 32) | 71.9% (23 out of 32) | 90.6% (29 out of 32) |
| MPS IVB | 0% (0 out of 4) | 0% (0 out of 4) | 0% (0 out of 4) |
| MPS VII | 100% (3 out of 3) | 66.7% (2 out of 3) | 100% (3 out of 3) |

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A method of detecting mucopolysaccharidosis IVA or mucopolysaccharidosis VII, or for monitoring the progress of mucopolysaccharidosis IVA or mucopolysaccharidosis VII, in a human subject, the method comprising:
    (a) providing a biological sample of about 10 μl comprising biological material, wherein the biological material contains glycosaminoglycans derived from the subject;
    (b) digesting the biological material with an enzyme that converts chondroitin 6-sulfate into ΔDi-6S;
    (c) performing one of the following steps:
        (i) detecting a level of ΔDi-6S and a level of keratan sulfate (KS) generated by said enzyme digestion of the biological material by liquid chromatography-tandem mass spectroscopy analysis for mucopolysaccharidosis IVA, or
        (ii) detecting the level of ΔDi-6S generated by said enzyme digestion of the biological material by liquid chromatography-tandem mass spectroscopy analysis for mucopolysaccharidosis VII; and
    (d) performing one of the following steps:
        (i) comparing the levels of both ΔDi-6S and KS generated from the biological material to the levels of ΔDi-6S and KS, respectively, in an age-matched control for mucopolysaccharidosis IVA, and determining mucopolysaccharidosis IVA affliction in the subject if the levels of both ΔDi-6S and KS generated from the biological material are elevated over the age-matched control,
        (ii) comparing the level of ΔDi-6S generated from the biological material to the level of ΔDi-6S in an age-matched control for mucopolysaccharidosis VII, and determining mucopolysaccharidosis VII affliction in the subject if the level of ΔDi-6S generated from the biological material is elevated over the age-matched control, or
        (iii) comparing the level of ΔDi-6S generated from the biological material to the level of ΔDi-6S generated by carrying out steps (b) and (c) on a biological material from the same subject taken at a later time point, comparing the level of KS in the biological material to the level of KS from the biological material from the same subject taken at the later point, and determining that the subject's mucopolysaccharidosis has progressed if the level of ΔDi-6S generated from the biological material taken at the later time point relative to the level generated from the biological material taken at the earlier time point is elevated and the level of KS is elevated at the later time point relative to the level of KS at the earlier time point.

2. The method according to claim 1, wherein the biological sample is blood, plasma, serum, urine or tissue.

3. The method according to claim 2, wherein the biological sample is dried blood.

4. The method according to claim 1 wherein the enzyme is chondroitinase C or chondroitinase ABC.

5. The method according to claim 1, wherein the subject is at least about 5 years of age.

6. The method according to claim 1, wherein the subject is a newborn.

7. The method according to claim 1, wherein the KS age-matched control and the ΔDi-6S age-matched control are from age-matched control subjects, or a single age-matched control subject.

8. The method according to claim 1, further comprising digesting the biological material with an enzyme that converts KS into Galβ1→4GlcNAc(6S), and comparing the level of said Galβ1→4GlcNAc(6S) generated from the biological material to the level of Galβ1→4GlcNAc(6S) in an age-matched control, and determining that the subject may be afflicted with mucopolysaccharidosis IVA if both the level of ΔDi-6S generated from the biological material is elevated over the age-matched control, and the level of Galβ1→4GlcNAc(6S) in said biological material is elevated over the age-matched control.

9. The method according to claim 8, wherein the enzyme is keratanase II.

10. The method according to claim 1, further comprising performing an N-acetylgalactosamine-6-sulfate sulfatase activity assay to confirm mucopolysaccharidosis IVA affliction in the subject.

11. The method according to claim 1, further comprising performing a genetic test for a mutation in the gene for N-acetylgalactosamine-6-sulfate sulfatase to confirm mucopolysaccharidosis IVA affliction in the subject.

12. The method according to claim 1, further comprising performing a β-D-glucuronidase activity assay to confirm mucopolysaccharidosis VII affliction in the subject.

13. The method according to claim 1, further comprising performing a genetic test for a mutation in the gene for β-D-glucuronidase to confirm mucopolysaccharidosis VII affliction in the subject.

14. The method according to claim 1, further comprising treating the subject for said mucopolysaccharidosis IVA or mucopolysaccharidosis VII.

15. The method according to claim 14, wherein said treatment comprises enzyme replacement therapy.

16. The method according to claim 14, wherein said treatment comprises hematopoietic stem cell transplantation.

17. The method according to claim 1 for monitoring the progress of mucopolysaccharidosis IVA or mucopolysaccharidosis VII, wherein step (d) comprises comparing the level of ΔDi-6S generated from the biological material to the level of ΔDi-6S generated by carrying out steps (b) and (c) on a biological material from the same subject taken at a later time point, and determining that the subject's mucopolysaccharidosis has progressed if the level of ΔDi-6S generated from the biological material taken at the later time point relative to the level generated from the biological material taken at an earlier time point is elevated.

18. The method according to claim 17, further comprising detecting the level of KS in said biological material, and comparing the level of KS in the biological material to the level of KS from the biological material from the same subject taken at the later time point, and determining progression of mucopolysaccharidosis in the subject if both the level of ΔDi-6S and the level of KS are elevated at the later time point relative to the levels of ΔDi-6S and KS at the earlier time point.

19. The method according to claim 17, further comprising digesting the biological material with an enzyme that converts KS into Galβ1→4GlcNAc(6S), and comparing the level of said Galβ1→4GlcNAc(6S) generated from the biological material to the level of Galβ1→4GlcNAc(6S) generated from the biological material from the same subject taken at the later time point, and determining progression of mucopolysaccharidosis in the subject if both the level of ΔDi-6S and the level of Galβ1→4GlcNAc(6S) are elevated at the later time point relative to the levels of ΔDi-6S and Galβ1→4GlcNAc(6S) at the earlier time point.

20. A method of monitoring the efficacy of a treatment of mucopolysaccharidosis IVA or mucopolysaccharidosis VII in a human subject, the method comprising:
(a) providing a biological sample of about 10 μl or less comprising biological material, wherein the biological material contains glycosaminoglycans derived from the subject at a time point during or after a course of therapy for said mucopolysaccharidosis IVA or mucopolysaccharidosis VII;
(b) digesting the material with an enzyme that converts chondroitin 6-sulfate into ΔDi-6S;
(c) performing one of the following steps:
(i) detecting a level of ΔDi-6S and a level of keratan sulfate (KS) generated by said enzyme digestion of the biological material by liquid chromatography-tandem mass spectroscopy analysis for mucopolysaccharidosis IVA, or
(ii) detecting the level of ΔDi-6S generated by said enzyme digestion of the biological material by liquid chromatography-tandem mass spectroscopy analysis for mucopolysaccharidosis VII; and
(d) performing one of the following steps:
comparing the levels of both ΔDi-6S and KS generated from the biological material to the level of ΔDi-6S generated by carrying out steps (b) and (c) on a biological material taken from the subject at an earlier time point before or during the course of therapy, comparing the KS level in the biological material to the KS level from a biological material from the same subject taken at the later point, and determining that the course of therapy is not likely efficacious in treating said mucopolysaccharidosis if the level of ΔDi-6S generated from the biological material taken at the later time point is elevated in comparison to the level of ΔDi-6S generated from the biological material taken at the earlier time point, and the KS level is elevated at the later time point relative to the KS level at the earlier time point.

21. The method according to claim 20, further comprising digesting the biological material with an enzyme that converts KS into Galβ1→4GlcNAc(6S), and comparing the level of said Galβ1→4GlcNAc(6S) generated from the biological material to the level of Galβ1→4GlcNAc(6S) generated from a biological material from the same subject taken at the earlier time point, and determining that the course of therapy is not likely efficacious in treating said mucopolysaccharidosis if both the level of ΔDi-6S and the level of Galβ1→4GlcNAc(6S) are elevated at the later time point relative to the levels of ΔDi-6S and Galβ1→4GlcNAc(6S) at the earlier time point.

22. The method according to claim 20, wherein said therapy comprises enzyme replacement therapy.

23. The method according to claim 20, wherein said therapy comprises hematopoietic stem cell transplantation.

24. The method according to claim 1, wherein the amount of biological sample provided is 10 μl.

25. The method according to claim 20, wherein the amount of biological sample provided is 10 μl.

* * * * *